(12) United States Patent
Steinemann

(10) Patent No.: US 7,161,116 B2
(45) Date of Patent: Jan. 9, 2007

(54) WELDING PROTECTIVE MASK WITH ILLUMINATION EQUIPMENT

(75) Inventor: Lukas Steinemann, Jona (CH)

(73) Assignee: Optrel AG, Wattwil (CH)

( * ) Notice: Subject to any disclaimer, the term of this patent is extended or adjusted under 35 U.S.C. 154(b) by 232 days.

(21) Appl. No.: 10/923,366

(22) Filed: Aug. 20, 2004

(65) Prior Publication Data
US 2005/0077278 A1   Apr. 14, 2005

(30) Foreign Application Priority Data
Sep. 2, 2003  (CH) .................................... 1501/03

(51) Int. Cl.
*B23K 9/32* (2006.01)
(52) U.S. Cl. .......................................... 219/147; 2/8.2
(58) Field of Classification Search ................ 219/147, 219/136; 2/8.2
See application file for complete search history.

(56) References Cited

U.S. PATENT DOCUMENTS

| | | | |
|---|---|---|---|
| 2,046,999 A * | 7/1936 | Bredtschneider | 219/136 |
| 3,227,866 A * | 1/1966 | Peters et al. | 219/147 |
| 4,332,004 A * | 5/1982 | Slaughter | 219/147 |
| 6,340,234 B1 * | 1/2002 | Brown, Jr. | 362/105 |
| 6,483,090 B1 * | 11/2002 | Bae | 2/8.8 |
| 6,733,150 B1 * | 5/2004 | Hanley | 362/106 |
| 2004/0240198 A1 * | 12/2004 | Van Laar et al. | 362/105 |

FOREIGN PATENT DOCUMENTS

| | | |
|---|---|---|
| DE | 20 25 847 A | 12/1970 |
| DE | 31 41 228 A | 4/1983 |
| DE | 31 41 228 A1 | 4/1983 |
| GB | 2 185 103 A | 7/1987 |
| GB | 2 369 194 A | 5/2002 |

* cited by examiner

*Primary Examiner*—Clifford C. Shaw
(74) *Attorney, Agent, or Firm*—Rankin, Hill, Porter & Clark LLP

(57) ABSTRACT

A welding protective mask (1) includes illumination equipment (3) for illuminating a work area. The illumination equipment (3) includes an illumination device (5), a detection device (8) for detecting an ambient light intensity, an energy storage (7) for electrically supplying the illumination equipment (3) and controller (6) for controlling an intensity of light radiated by the illumination means (5) according to the ambient light intensity. In a preferred embodiment of the invention the controller (6) is set up to detect a welding process with a flicker circuit and to switch off the illumination device (5) during the welding process.

11 Claims, 2 Drawing Sheets

WELDING PROTECTIVE MASK WITH ILLUMINATION EQUIPMENT

The invention relates to a welding protective mask with illumination equipment as well as an adaptor for the mounting of the illumination equipment.

BACKGROUND OF THE INVENTION

In car manufacturing or ship construction it is for example usual to arrange lights for the illumination of the work area of a welder. This involves a great effort for installation and cabling. A welding protective mask with its own illumination equipment is known for example from DE 31 41 228. To the welding protective mask a halogen lamp is fastened, and fed by a transformer or a welding device through a cable and a foot- or manual switch. Even with this type of lighting, a cable for feeding the lamp is necessary, which makes the use of the lamp laborious.

DESCRIPTION OF THE INVENTION

It is therefore an object of the invention to create a welding protective mask of the type mentioned initially, which overcomes the disadvantages of the state of the art. It is furthermore an object of the invention to create corresponding illumination equipment and an adaptor for the mounting of the illumination equipment.

The inventive welding protective mask comprises illumination equipment with an illumination means, a detection means detecting an intensity of ambient light, an energy storage device supplying the illumination equipment electrically, and a control means for controlling an intensity of a light radiated by the illumination means e.g. in accordance with the ambient light intensity.

Thus, owing to the energy storage device, it becomes possible to operate the illumination equipment without cabling to a power supply separated from the mask, in which through controlling the light intensity, the energy consumption is reduced compared to continuous operation with constant light intensity.

In a preferred variant of the invention, the control means are set up to reduce the intensity of the radiated light when the ambient light intensity increases. This may happen in various ways. The intensity of the radiated light is, for an increasing intensity of ambient light, reduced monotonously and/or step-wise to a zero value.

In a preferred embodiment of the invention the illumination means is switched off, if the detected intensity of ambient light exceeds a preset value, or if a flicker circuit detects a welding process. Thus, on the one hand it is ensured that there is a sufficient illumination of the work area, and on the other hand the energy storage will not be strained without necessity.

The illumination means comprises preferably one or several light emitting diodes, especially white or blue light-emitting diodes. Thus, the energy consumption of the illumination equipment is reduced further. The light emitting diodes are operated in a pulsed manner for further energy saving, which is possible within certain limits without a decrease of their perceived luminous intensity. If the intensity of the light radiated from the light emitting diodes has to be adjusted, this preferably happens by changing the voltage, with which the light emitting diodes are controlled. For a pulsed triggering preferably a modulation of the pulse is carried out through pulse width- or pulse repetition frequency modulation.

In an additional preferred variant of the invention, the illumination equipment is created as detachable unit, especially as mechanically independent constructional unit and as electrically autonomous unit. This unit thus comprises the energy storage device, the detection means, the control means and the illumination means. The unit may be inserted for use into the welding protective mask.

The illumination equipment created as an independent unit is preferably insertable into an adaptor for the mounting of a glare protection device in the welding protective mask. This insertion happens for example through a clip-on- or snap-in connection, or with the help of slideable locking elements, that can be engaged and disengaged again by hand. A glare protection device is a Wood's glass or an electro-optical unit. The electro-optical unit with when in normal condition a transparent eye-protecting lens stands out by the fact that, when detecting an electric arc, the eye-protecting lens automatically is darkened and the welder is protected from the dazzlement. Modern glare protection devices comprise energy storage accumulators or batteries, supplied by solar cells, so they do not have to be charged by other means. The detection of an electric arc happens in a well-known way with a so-called flicker circuit, as it can also be used in the present invention. Such a flicker circuit detects the occurrence of a welding process owing to characteristic qualities of the then occurring and measured light intensity, for example owing to a high share of signals in the frequency range higher than 200 Hz. In order to combine glare protection devices and welding protective masks of different construction, mechanical adaptors are used, and these mechanical adapters establish a light proof as well as positive locked and frictional mechanical connection. The arrangement of the illumination equipment in such an adaptor therefore permits also a flexible use in different protective masks and a simple interchangeability of the illumination equipment.

The illumination equipment also may be integrated mechanically and/or electrically into a glare protection device. In the case it is integrated mechanically, both are replaceable together. In the case it is integrated electrically, the power supply and/or the light detection and especially the flicker circuit may be used together. With this electrical integration, the illumination equipment nevertheless can be created as a separate mechanical constructional unit. The illumination equipment in this case is connected with the glare protection device by a fixed or disconnectable signal wire connection. The glare protection device is set up for the transmission of a measuring signal according to the detected light intensity, or a switch signal to the illumination equipment, as soon as the glare protection device detects an electric arc. In the simplest case, control electronics of the glare protection device operate a contact, by which the illumination means are supplied.

The detection means and the illumination means, or the complete, independent unit, may be arranged, for example, in a forehead area or a chin area of the welding protective mask. Preferably they are arranged behind the same front pane as the glare protection device. Such exchangeable front panes usually are used as protection for the glare protection devices against sparks and slag. By this arrangement of the illumination equipment, a separate protection for the detection means and the illumination means, which also would have to be exchangeable, is superfluous. Thus, the construction of the welding protective mask according to the invention is simplified.

In a preferred variant of the invention, the illumination equipment comprises a push-button, by which the turning on or rather the putting into service of the illumination equipment is realized by pressing the button. With another pressing of the button, the illumination equipment is switched off again. The button may be arranged on the illumination equipment itself or, via an electrical connection, removed to, for example, a temple area of the welding protective mask. The illumination equipment preferably is switched off automatically, if during a predetermined time no elevated light intensity is detected, or especially if the flicker circuit does not respond. Thus, discharging of the energy storage device is avoided, if by mistake the illumination equipment is not switched off.

Illumination equipment according to the invention is planned for use in a welding protective mask according to the invention. This illumination equipment therefore comprises the properties mentioned above in connection with the welding protective mask. Preferably it is created as electrically and/or mechanically independent constructional unit and is insertable into the adaptor.

An adaptor according to the invention is configured to receive or hold the illumination equipment according to the invention into a welding protective mask.

BRIEF DESCRIPTION OF THE DRAWINGS

The subject matter of the invention will be explained in more detail in the following text with reference to preferred exemplary embodiments, which are illustrated in the attached drawings, in which.

The reference symbols used in the drawings, and their meanings, are listed in summary form in the list of reference symbols. In principle, identical parts are provided with the same reference symbols in the figures.

DETAILED DESCRIPTION OF PREFERRED EMBODIMENTS OF THE INVENTION

Figure 1:
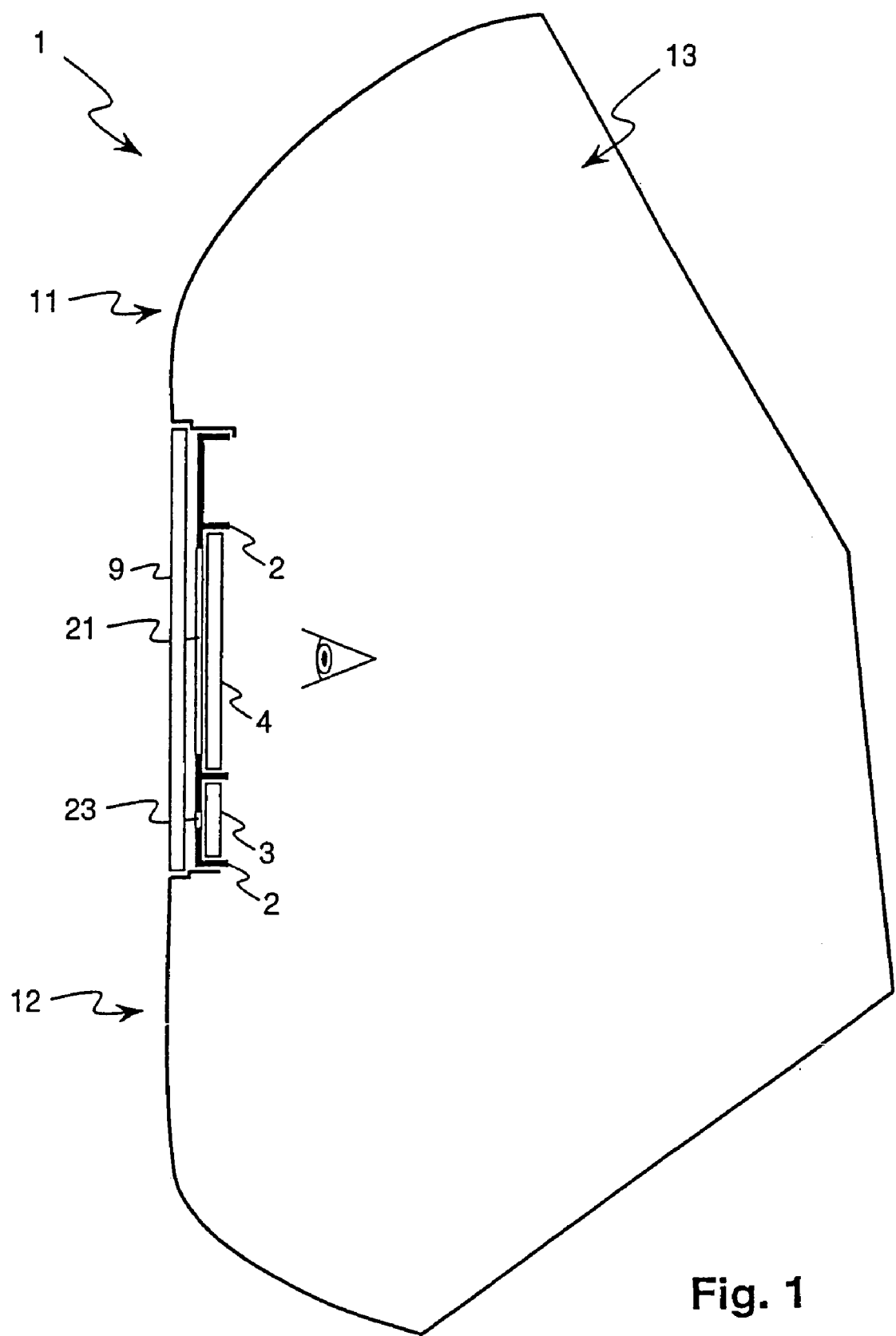
FIG. 1 schematically shows a cross-section of a welding protective mask according to the invention.

FIG. 1 schematically shows a cross-section of a welding protective mask according to the invention. The welding protective mask 1 comprises an adaptor 2 for mounting a glare protection device 4 and illumination equipment 3 according to the invention. The adaptor 2 and consequently also the glare protection device 4 and the illumination equipment 3 are arranged behind an exchangeable front pane 9. Details of the mounting of the adaptor 2 and front pane 9 as well as glare protection device 4 and illumination equipment 3 are not drawn in.

Figure 2:
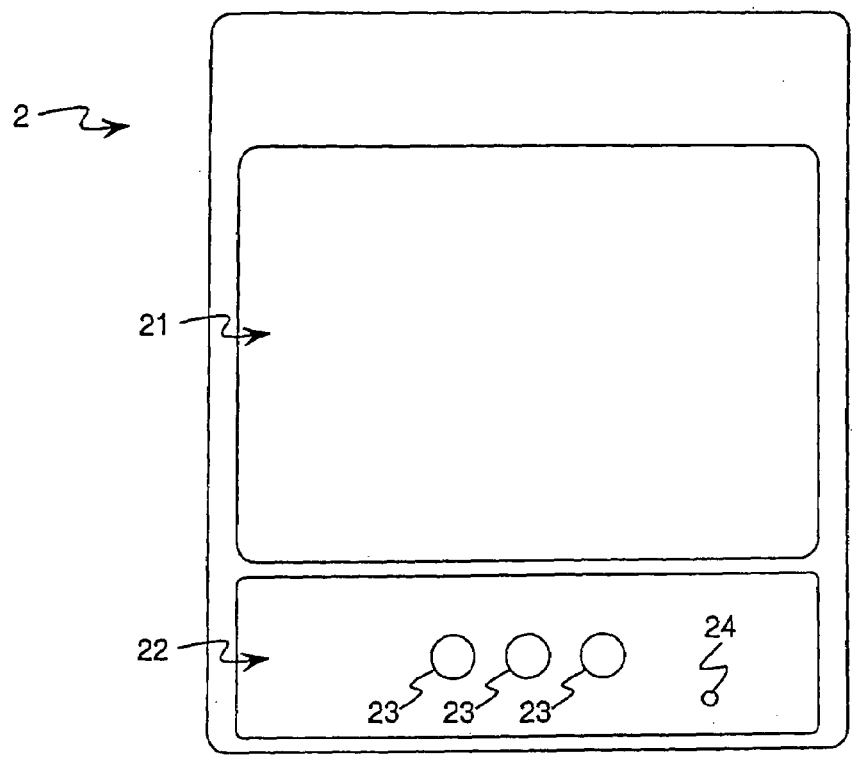
FIG. 2 schematically shows a top-view on an adaptor according to the invention.

FIG. 2 schematically shows a top view on an adaptor 2 according to the invention. The adaptor 2 comprises an opening 21 for inserting the glare protection device 4 and a recess 22 for plugging in the illumination equipment 3. In the recess 22 for plugging in the illumination equipment 3 one or several openings 23 are arranged, in this case three, for illumination means, especially light emitting diodes 5, as well as at least one opening 24 for detection means 8. The adaptor 2 comprises bulges or indentations and snap-connections, or revolving, or movable lock elements for detachable mechanical connection of the adaptor 2 with the mask, the illumination equipment 3 and the glare protection device 4.

Figure 3:
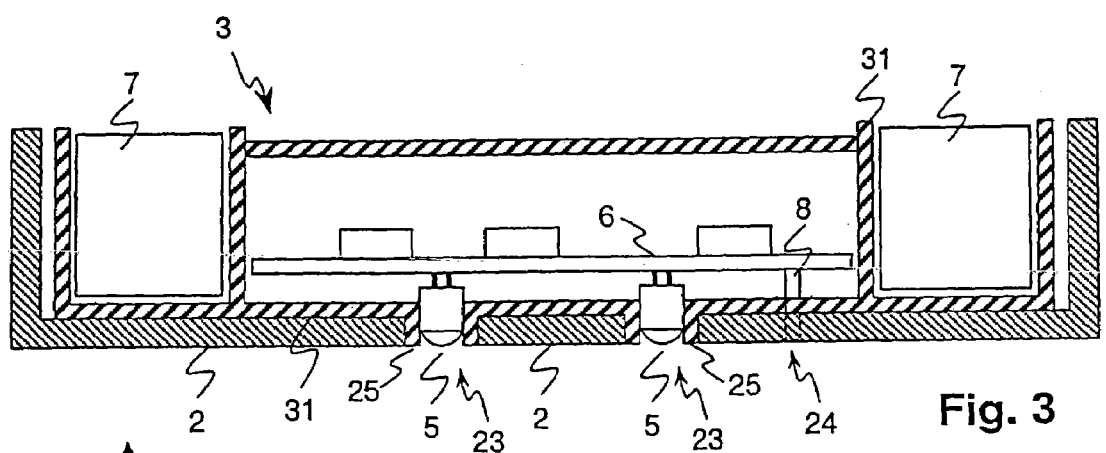
FIG. 3 schematically shows a cross-section of an illumination equipment inserted in an adaptor.

FIG. 3 schematically shows a cross-section through an illumination equipment 3, created as independent unit, and inserted into an adaptor 2. The cross section plane runs vertically to the image plane of FIG. 2 and through the several openings 23. A variant with two openings 23 and light emitting diodes 5 each is described. The illumination equipment 3 is for example inserted detachably into the adaptor 2 with a snap-connection. Correct insertion of the illumination equipment 3 into the adaptor is preferably given, when the side-by-side borders are level. The illumination equipment 3 comprises an electronic circuit 6 as a control unit. One or several preferably blue or white light emitting diodes 5 are used as illumination means. They preferably are soldered onto a printed circuit board of the electronic circuit 6 and stick out through corresponding openings in a covering 31 of the electronic circuit 6. Around these openings, collars 25 in the covering 31 are shaped. These collars 25 each correspond to assigned openings 23 of the adaptor 2, such that lightproof terminals result when inserting the illumination equipment 3 into the adaptor 2. The collars 25 can be metallised and shaped as reflectors. The covering 31 preferably is a casing of the illumination equipment 3 and, for example, formed as an injection moulded part made of synthetic material. The covering also can be shaped by encapsulating at least the electronic circuit 6 and the light emitting diodes 5 with synthetic material.

A photocell 8 acting as detection means, like for example a silicon photosensor, lies in FIG. 3 behind the cutting plane. The covering 31 and the adaptor 2 comprise corresponding openings, so that the photocell 8 can receive light from the work area of the welding protective mask 1.

An adaptor 2 comprises one or several batteries 7 as energy storage devices. A battery is either separately removeable and replaceable or rechargeable, or else the entire illumination equipment 3 comprises an electrical connection for charging the batteries 7. Optionally the illumination equipment 3 comprises solar cells as support for charging the batteries. In a variant as independent unit, corresponding openings for the solar cells are shaped in the adaptor.

Figure 4:
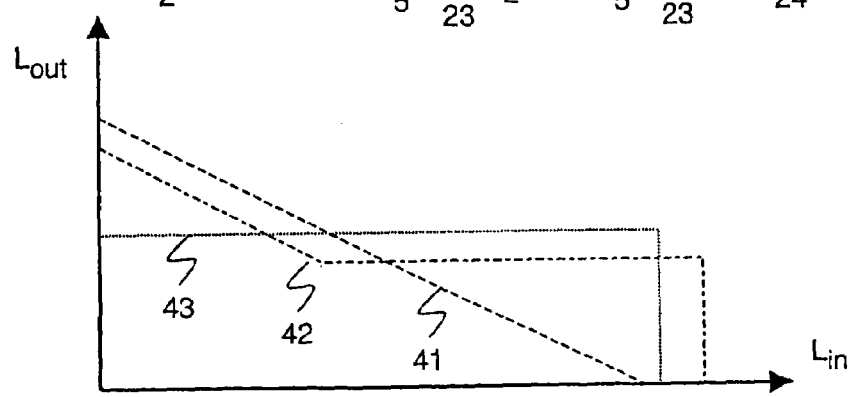
FIG. 4 various trajectories of the intensity of radiated light in dependence of a detected ambient light intensity.

FIG. 4 shows different preferred trajectory of the intensity of a radiant light $L_{out}$ in dependency of a detected ambient light intensity $L_{in}$. According to a first trajectory, the intensity of the radiant light starting from maximal intensity is reduced monotonously to a zero value for an increasing intensity of ambient light.

According to a second trajectory 42, the intensity of the radiant light starting from a maximal intensity is reduced monotonously to a preset value for an increasing ambient light intensity, then is maintained constant, and when reaching a further preset value, is set to zero.

The continuous control or decrease of the radiant light intensity occurs through modulation of a supply voltage of the light emitting diodes, and/or through a pulsed supply with a pulse-width modulation or pulse frequency modulation. Due to the pulse modulation in a definite range, an energy saving in a certain range is possible, with essentially constant luminosity.

According to a third trajectory 43, the intensity of the radiant light is maintained constant for a growing intensity of ambient light, and is set to zero when exceeding a defined threshold value, or when a flicker circuit responds. It is also possible to control the light intensity according to the first or second trajectory 41, 42, and to use the flicker circuit only to switch off the illumination equipment 3 in the case of a longer absence of a welding process.

A button or a switch to turn on and turn off the illumination equipment 3 is arranged for example at a temple area 13 of the welding protective mask 1 and is, by means of a wire connection, operationally connected to the other components of the illumination equipment 3.

While the invention has been described in present preferred embodiments of the invention, it is distinctly understood that the invention is not limited thereto, but may be otherwise variously embodied and practised within the scope of the claims.

LIST OF REFERENCE SYMBOLS

1 Welding protective mask
2 Adaptor
3 Illumination equipment
4 Glare protection device
5 Illumination means, light emitting diodes
6 Control means, electronic circuit
7 Battery
8 Detection means, photo cell
9 Front pane
11 Forehead area
12 Chin area
13 Temple area
21 Opening for inserting the glare protection device
22 Recess for inserting the illumination equipment
23 Openings for the illumination means
24 Opening for the detection means
25 Collar
31 Covering
41 First trajectory
42 Second trajectory
43 Third trajectory

The invention claimed is:

1. A welding protective mask (1) with illumination equipment (3) for illuminating a work area, wherein the illumination equipment comprises illumination means (5), detection means (8) for detecting an ambient light intensity, an energy storage device (7) for supplying electricity to the illumination equipment (3) and control means (6) for controlling an intensity of light radiated by the illumination means (5) by detecting the ambient light intensity, including light from a welding process, through a flicker circuit, and switching off the illumination means (5) during the welding process.

2. The welding protective mask (1) according to claim 1, wherein the control means (6) are set up to reduce the intensity of the radiated light with increasing ambient light intensity.

3. The welding protective mask (1) according to claim 1 wherein the illumination means (5) comprises at least one light emitting diode (5) and the control means (6) are set up to control the at least one light emitting diode (5) through variation of a DC voltage.

4. The welding protective mask (1) according to claim 1 wherein the illumination means (5) comprises at least one light emitting diode (5) and the control means (6) are set up to control the at least one light emitting diode (5) through pulse modulation.

5. The welding protective mask (1) according to claim 1 wherein the illumination equipment (3) is created as a detachable unit.

6. The welding protective mask (1) according to claim 5, wherein the illumination equipment (3) is exchangeably inserted into an adaptor (2) for mounting a glare protection device.

7. The welding protective mask (1) according to claim 1 wherein the illumination equipment (3) comprises a button for turning on the illumination equipment (3) and is set up for automatic turning off of the illumination equipment if during a preset time no welding process is detected.

8. Illumination equipment (3) for use in a welding protective mask (1) according to claim 1.

9. An adaptor for mounting illumination equipment (3) according to claim 8 in a welding protective mask (1).

10. The welding protective mask (1) according to claim 1, wherein the control means are set up to reduce the intensity of the radiated light in a step-wise manner to a zero value when the ambient light intensity increases.

11. The welding protective mask (1) according to claim 1, wherein the illumination means comprises several white or blue emitting diodes operated in a pulsed manner.

* * * * *